United States Patent
Fatiny et al.

(10) Patent No.: US 10,327,871 B2
(45) Date of Patent: Jun. 25, 2019

(54) REINFORCED GINGIVAL RETRACTION CORD

(71) Applicant: King Abdulaziz University, Jeddah (SA)

(72) Inventors: Fahad Ibrahim Fatiny, Jeddah (SA); Mohammed A. Wahbi, Jeddah (SA); Turki Y. Alhazzazi, Jeddah (SA); Yaser M. Alkhiary, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 15/248,736

(22) Filed: Aug. 26, 2016

(65) Prior Publication Data
US 2018/0055610 A1  Mar. 1, 2018

(51) Int. Cl.
*A61C 9/00* (2006.01)
*A61C 3/08* (2006.01)

(52) U.S. Cl.
CPC .............. *A61C 9/0033* (2013.01); *A61C 3/08* (2013.01)

(58) Field of Classification Search
CPC .......................... A61C 9/0033; A61C 15/041; A61C 15/046; A61C 7/12; A61C 7/20; A61C 7/28; A61C 15/04–043; A61Q 11/00
USPC ......................................................... 433/136
See application file for complete search history.

(56) References Cited

U.S. PATENT DOCUMENTS

| | | | | |
|---|---|---|---|---|
| 4,321,038 A | * | 3/1982 | Porteous | A61C 9/0033 433/136 |
| 4,366,206 A | * | 12/1982 | Tanaka | A61C 9/0033 428/364 |
| 4,374,175 A | * | 2/1983 | Tanaka | A61C 9/0033 428/369 |
| 4,465,462 A | * | 8/1984 | Ticknor | A61C 9/0033 433/136 |
| 4,522,593 A | * | 6/1985 | Fischer | A61C 9/0033 433/136 |
| 4,585,414 A | * | 4/1986 | Kottemann | A61C 7/20 433/20 |
| 4,659,310 A | * | 4/1987 | Kottemann | A61C 7/20 433/20 |
| 4,869,666 A | * | 9/1989 | Talass | A61C 7/20 433/20 |
| 4,871,311 A | * | 10/1989 | Hagne | A61C 9/0033 433/136 |
| 4,892,482 A | * | 1/1990 | Lococo | A61C 9/0033 433/136 |
| 5,063,948 A | | 11/1991 | Lloyd | |
| 5,413,127 A | * | 5/1995 | Hill | A61C 15/041 132/321 |

(Continued)

FOREIGN PATENT DOCUMENTS

EP  1839618 A1  10/2007

*Primary Examiner* — Wade Miles
*Assistant Examiner* — Shannel N Wright
(74) *Attorney, Agent, or Firm* — Oblon, McClelland, Maier & Neustadt, L.L.P.

(57) ABSTRACT

A dental retraction elongated member, for example, a retraction cord, for placement between a tooth and its adjacent gum tissue during dental impression taking and restorative procedures includes a core coated with a thermoplastic material so that the retraction cord is resistant to shredding, tearing, and sticking to dental restorative and impression taking materials.

20 Claims, 6 Drawing Sheets

(56) References Cited

U.S. PATENT DOCUMENTS

| | | | | |
|---|---|---|---|---|
| 5,454,716 A * | 10/1995 | Banerjee | A61C 7/20 | 433/20 |
| 5,527,181 A * | 6/1996 | Rawls | A61O 5/88 | 433/136 |
| 5,540,588 A * | 7/1996 | Earle | A61C 9/0033 | 433/136 |
| 5,573,850 A * | 11/1996 | Cunningham | D01D 11/06 | 428/370 |
| 5,718,251 A * | 2/1998 | Gray | A61B 17/06166 | 132/321 |
| 5,899,694 A * | 5/1999 | Summer | A61C 9/0033 | 433/136 |
| 6,039,054 A * | 3/2000 | Park | A61C 15/041 | 132/321 |
| 6,299,448 B1 | 10/2001 | Zdrahala et al. | | |
| 6,333,374 B1 * | 12/2001 | Chen | A61C 15/00 | 524/270 |
| 6,375,461 B1 * | 4/2002 | Jensen | A61C 9/0033 | 433/136 |
| 6,814,086 B2 | 11/2004 | Stallings | | |
| 7,159,259 B2 * | 1/2007 | Chen | A01K 97/045 | 264/109 |
| 7,883,335 B2 | 2/2011 | Fischer et al. | | |
| 2004/0126740 A1 | 7/2004 | Coopersmith | A61C 9/0033 | 433/136 |
| 2004/0265777 A1 * | 12/2004 | Heasley | A61C 9/0033 | 433/136 |
| 2005/0171492 A1 * | 8/2005 | Rodriquez | A61M 5/14 | 604/264 |
| 2005/0277087 A1 * | 12/2005 | Dds | A61C 9/0033 | 433/136 |
| 2005/0277088 A1 * | 12/2005 | Fischer | A61C 9/0033 | 433/136 |
| 2007/0231773 A1 * | 10/2007 | Pontynen | A61C 17/04 | 433/140 |
| 2008/0003538 A1 * | 1/2008 | Wittrock | A61C 9/0033 | 433/136 |
| 2008/0051829 A1 * | 2/2008 | Eidenschink | A61B 17/0057 | 606/213 |
| 2008/0096164 A1 * | 4/2008 | Fischer | A61C 9/0033 | 433/136 |
| 2008/0269420 A1 * | 10/2008 | Tong | B29C 61/003 | 525/208 |
| 2009/0017420 A1 * | 1/2009 | Jabri | A61C 3/02 | 433/136 |
| 2009/0098501 A1 * | 4/2009 | Klettke | A61C 9/0033 | 433/8 |
| 2009/0131557 A1 * | 5/2009 | Uyama | C08L 27/06 | 523/400 |
| 2010/0261143 A1 * | 10/2010 | Hampe | A61K 6/0011 | 433/215 |
| 2011/0054351 A1 * | 3/2011 | Fox | A61L 27/06 | 600/585 |
| 2011/0097686 A1 * | 4/2011 | Ross | A61C 9/0033 | 433/138 |
| 2011/0217670 A1 * | 9/2011 | Walter | A61C 9/0033 | 433/82 |
| 2011/0229849 A1 * | 9/2011 | Maurer | A61C 9/0033 | 433/136 |
| 2012/0180802 A1 * | 7/2012 | Ware | A61L 31/04 | 128/898 |
| 2012/0196246 A1 * | 8/2012 | Drapeau | A61C 9/0033 | 433/138 |
| 2013/0183630 A1 * | 7/2013 | Krikorian | C09J 159/00 | 433/3 |
| 2013/0193154 A1 * | 8/2013 | Moore | A61C 9/0033 | 221/1 |
| 2013/0264332 A1 * | 10/2013 | Auffinger | H05B 3/10 | 219/548 |
| 2014/0087330 A1 * | 3/2014 | Discko | A61C 9/0033 | 433/136 |
| 2014/0170596 A1 * | 6/2014 | Angeletakis | A61K 6/0067 | 433/136 |
| 2016/0058585 A1 * | 3/2016 | Seddon | A61F 2/90 | 623/1.28 |

\* cited by examiner

REINFORCED GINGIVAL RETRACTION CORD

BACKGROUND OF THE INVENTION

Field of the Invention

This disclosure relates to an intraoral dental retraction cord. More particularly, this disclosure relates to a gingival retraction cord which displaces the sulcus of the tooth and is resistant to shredding and tearing.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Current dental practices make use of intraoral dental retraction cords during both restorative and impression taking operations (i.e. prosthetic dentistry). Such cords are often referred to as gingival tissue retraction cords.

When restoration of dental caries (cavities) at, near, or below the marginal attached gingiva (gum line) is required, dentists typically distend and retract the gingival or periodontal sulcus (eyelid-like space below the top of the gum line) in order to achieve sufficient access to the carious lesion. Thereafter, the practitioner generally removes the dental caries by drilling and fills the cleaned out hole in the tooth with a visible light cure (VLC) composite resin or amalgam.

The distention of the periodontal sulcus is typically achieved with a rubber dam and a corresponding clamp. Alternatively a conventional woven or braided gingival retraction cord is used. A significant drawback associated with the use of a rubber dam and corresponding clamp(s) is that they often produce periodontal tissue trauma and bleeding which compromise the restorative result. The problems which arise with the use of conventional woven or braided cords are discussed below.

Prosthetic dentistry is known in the art to involve the construction of crowns, caps, partial dentures, full dentures, implants, and fixed bridgework. The practice of prosthetic dentistry often requires the taking of accurate impressions (or molds) of a particular tooth, teeth, or implant for which prosthetics will be fabricated at a dental laboratory. At the interface (or limit line) of the tooth (or root, or implant) surface to be worked on and the gingival margin (gum line), it is important that prior to taking an impression, the gingival sulcus be retracted in order to register an accurate impression of the prepared tooth (or root, or implant) structure.

This type of retraction is typically accomplished with a conventional dental periodontal sulcular retraction cord (or gingival retraction cord). In short, a small diameter (e.g. 1-2 mm) braided or woven cotton cord is pressed into the periodontal sulcus prior to flowing the impression material onto the tooth, teeth, or implant. Conventional retraction cord is often impregnated with certain chemicals (e.g. racemic epinephrine, aluminum chloride, or adrenalin).

In use, this conventional retraction cord is typically unwound from a spool or withdrawn from a container. The dental practitioner estimates the length of cord required for the particular application and snips the desired length of cord from the spool. The practitioner then wraps the cord around the tooth and either ties a knot to hold the cord in position on the cervical portion of the tooth, or overlays several turns of the cord on the tooth to hold the cord in place. The practitioner then packs the cord into the gingival sulcus so as to retract the gum tissue away from the tooth structure thereby enabling the accurate taking of an impression of the tooth inclusive of its cervical portion in prosthetic dentistry.

Practitioners often use small conventional dental instruments to position the cord in the periodontal space. Once the impression material hardens and is removed from the tooth and mouth or the filling is in place, the retraction cord is removed from the periodontal space and discarded. It is noted that the "periodontal space," "periodontal sulcus," "marginal periodontal tissue," and "gingival sulcus" are synonymous terms well-known in the art, and their well-known meaning is adopted here.

Problems arise in the use of these woven or braided cords whether used in the process of drilling and filling dental caries or in the other processes discussed above. For example, it is often the case that the insertion and removal of conventional woven or braided string-like gingival retraction cord produces gingival tissue trauma and periodontal sulcular bleeding thereby compromising the accuracy of the impression or filling and causing post-operative discomfort to the patient. Furthermore, some patients are chemically sensitive to conventional chemically impregnated retraction cords and experience discomforting side effects as a result thereof.

Another problem associated with conventional woven or braided string-like dental retraction cords is their tendency to physically attach or stick to dental restorative and impression taking materials. When such sticking occurs, it becomes extremely difficult for the practitioner to remove the cord from the periodontal sulcus and the finished restoration and/or impression taking material.

Yet another problem with conventional string-like woven or braided retraction cords is their tendency to shred or tear during both insertion and removal from the periodontal sulcus. Such shredding and tearing often produces undesirable gingival sulcular tissue trauma, bleeding, and post-operative patient discomfort. Additionally, torn or shredded pieces of the cord may be left behind inside the patient's mouth or gum line leading to the possibility of infection.

U.S. Pat. No. 4,892,482 discloses a gingival tissue dental retraction cord made of a plurality of strands including a central stiffener strand of, for example, copper wire or other material which provides the cord with deformability. Unfortunately, the construction of the dental retraction cord of this patent renders it subject to the above-mentioned disadvantages associated with other conventional retraction cords.

U.S. Pat. No. 4,871,311 discloses a dental retraction cord for uncovering and draining the preparation limit line of a tooth where the tooth emerges from the gum tissue during dental procedures such as the taking of dental impressions, the cementing of crowns, and the performance of conservative caries therapy. The retraction cord of this patent, after being inserted into the periodontal sulcus, swells and thereby mechanically uncovers the preparation limit line and tends to stop bleeding of the gum tissue. The preferred material for making the swelling cord of this patent is a super absorbent swelling material made of an acrylic fiber having a skin constituted by a co-polymer of polyacrylic acid and polyammonium acrylate and a core of polyacrylonitrile, in which the skin provides about thirty percent of the weight of the fiber. The cord of this patent, both before and after swelling, is susceptible to the disadvantages and problems set forth above.

U.S. Pat. No. 4,321,038 discloses a braided gingival retraction cord which is subject to the above-described disadvantages. The cord of this patent includes strands of fluid absorbent yarns or thread, such as cotton. Following fabrication, the braided cord of U.S. Pat. No. 4,321,038 is passed through a chemically impregnating solution containing a concentration of such chemicals as epinephrine, alum, aluminum chloride, or mixtures thereof, to saturate the cord.

U.S. Pat. No. 5,033,488 discloses a porous, high strength dental floss made of expanded polytetrafluoroethylene (i.e. PTFE or TEFLON™). The dental floss of this patent, coated with microcrystalline wax, is made using expanded PTFE (e-PTFE) so as to allow the dental floss to pass smoothly through the narrow spaces defined between adjacent teeth.

It is also known to use PTFE in clinical dentistry for periodontal regeneration surgical procedures. For example, GORE-TEX™ e-PTFE is often applied to periodontal osseous defects such as those which can occur around molar teeth or endosseous implants. Such material is used to guide regeneration of new bone around teeth or dental implants.

This GORE-TEX™ material is also used for guided tissue regeneration by draping the material over a surgically exposed tooth and cleansed periodontal site (e.g. a Class I furcation defect) so as to allow for regrowth of healthy periodontal tissue. Periodontal regeneration often occurs in this space. After removal of the PTFE material, newly regenerated periodontal fibers provide additional tooth support. These uses of e-PTFE, however, are not related to gingival retraction cord.

In view of the foregoing, one objective of the present disclosure is to provide a dental retraction cord which (1) is resistant to shredding and tearing, (2) is resistant to sticking to dental restorative and impression taking materials, (3) reduces tissue trauma, bleeding, and post-operative patient discomfort, and (4) displaces and conforms to the sulcus of the tooth to allow sufficient access to carious lesions, near, or below the gum line, thereby allowing impression taking material to capture the details of the tooth preparation. Furthermore, a need arises in the art for a dental retraction cord free of chemical impregnation so as to permit the cord to be used during dental procedures carried out upon chemically sensitive patients.

SUMMARY OF THE DISCLOSURE

The foregoing description is intended to provide a general introduction and summary of the present disclosure and is not intended to be limiting in its disclosure unless otherwise explicitly stated. The various embodiments, together with further advantages, will be best understood by reference to the following detailed description taken in conjunction with the accompanying drawings.

A first aspect of the disclosure relates to a flexible dental retraction elongated member placeable between a tooth and its adjacent gum tissue to retract the gum tissue from the tooth, comprising a core comprising a metal, a polymer, or mixtures thereof, and a thermoplastic which coats the core, which reinforces the thermoplastic, where the dental retraction elongated member is bendable, remains bent after being placed between the tooth and its adjacent gum tissue, is not chemically impregnated, a ratio of the diameter of the dental retraction elongated member to the diameter of the core is in a range of 7:6 to 10:1, and the diameter of the dental retraction elongated member is at most 10% of a length of the dental retraction elongated member.

In one embodiment, the diameter of the dental retraction elongated member is in a range of 0.5-3.0 mm.

In one embodiment, the dental retraction elongated member has a circular cross-section or an oval cross-section.

In one embodiment, the dental retraction elongated member has a circular cross-section.

In one embodiment, the thermoplastic is irreversibly attached to the core.

In one embodiment, the thermoplastic is polytetrafluoroethylene, polyester, or nylon.

In one embodiment, the thermoplastic comprises a photo-activated shape-memory polymer.

In one embodiment, the thermoplastic comprises a polymer which swells upon contact with a liquid.

In one embodiment, the core has a diameter in a range of 0.25-2.1 mm.

In one embodiment, the metal is present, and the metal is silver, copper, aluminum, steel, or mixtures thereof.

In one embodiment, the core is a single strand of metal wire or a braided metal wire.

In one embodiment, the core is a single strand of metal wire.

In one embodiment, the polymer is present, and the polymer is rubber, poly(methyl methacrylate), polyvinyl chloride, or mixtures thereof.

In one embodiment, the polymer is rubber.

In one embodiment, the core comprises a plurality of strands of the metal, a plurality of strands of the polymer, or both, which are woven, braided, or twisted together.

In one embodiment, a diameter of the strands is in a range of 0.05-0.15 mm.

A second aspect of the disclosure relates to a dental kit, comprising the dental retraction elongated member of the first aspect and a retraction cord packer.

DETAILED DESCRIPTION OF THE DISCLOSURE

Figure 1:
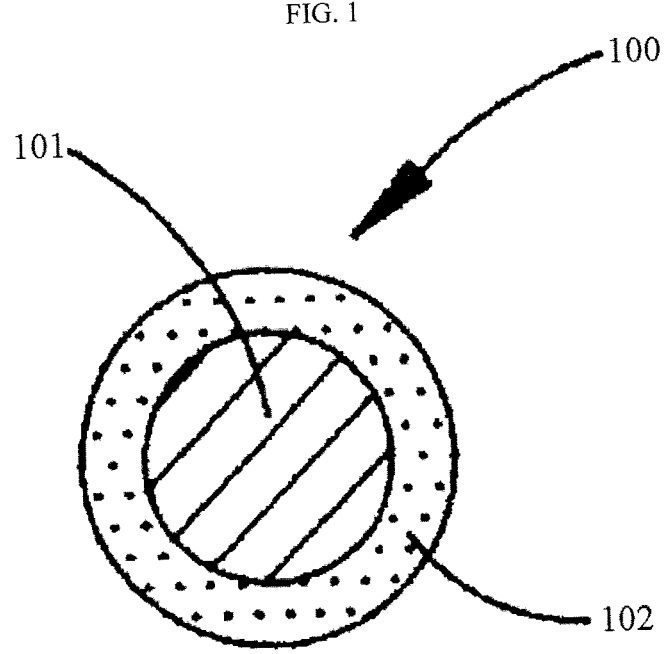
FIG. 1 is a cross-sectional view of an embodiment of a dental retraction elongated member.
Figure 2:
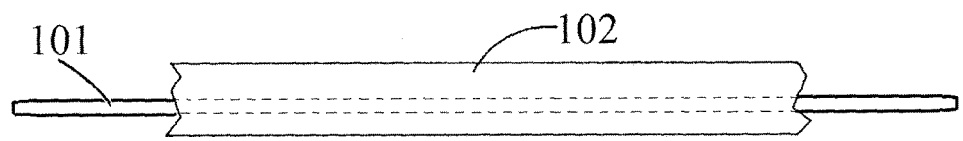
FIG. 2 is a side view illustrating the elongated body of an embodiment of a dental retraction elongated member.

Embodiments of the present disclosure will now be described more fully hereinafter with reference to the accompanying drawings, in which some, but not all embodiments of the disclosure are shown.

As used herein, the term "dental retraction elongated member" (e.g., "retraction device") refers to a retraction cord 100, which is shown for example in FIGS. 1-5. The retraction cord 100 comprises a central core 101 with an outer surface coated with a thermoplastic 102, e.g., a thermoplastic coating. The core 101 reinforces the thermoplastic 102. As used herein, the term "reinforce" refers to the presence of the core 101 to increase the stiffness of the retraction device relative to the thermoplastic 102 alone. As used herein, the term "stiffness" refers to the rigidity of an object and the extent to which it resists deformation in response to an applied force. The Young's modulus, a measure of stiffness, of the retraction cord 100 may range from 1-100 GPa, preferably 5-50 GPa, more preferably 5-20 GPa.

In one embodiment, the thermoplastic 102 is attached to the core 101 with one or more adhesives such as a collagen-based adhesive (e.g. an adhesive comprising porcine collagen, poly(L-glutamic), and water-soluble carbodiimides), a plant-based adhesive (e.g. gum Arabic, Canada balsam, latex, and starch), a silicone (e.g. polydimethylsiloxane and decamethyl cyclopentasiloxane), and an epoxy (e.g. bisphenol A epoxy, bisphenol F epoxy, glycidylamine epoxy, and novolac epoxy resin). The adhesive may be applied onto the outer surface of the core 101 before coating the thermoplastic 102. In one embodiment, the thermoplastic 102 is irreversibly attached to the core 101 with the use of the aforementioned adhesives. For example, there is cross-linking between the core 101 and the thermoplastic 102. As used herein, the term "irreversibly attached" means the thermoplastic 102 cannot be peeled/stripped from the core without damaging the thermoplastic 102, the core 101, or both.

The provision of the thermoplastic 102 results in the retraction cord 100 having a smooth outer or contacting surface. The average surface roughness ($R_a$) of the retraction cord 100 is in a range of 0.01-10 µm, preferably 0.01-5 µm, more preferably 0.01-2 µm, and $R_z$ of the retraction cord 100 is in a range of 0.05-40 µm, preferably 0.05-20 µm, more preferably 0.05-8 µm. As used herein, the term "$R_z$" refers to the average distance between the highest peak and the lowest valley in a sampling length according to American Society of Mechanical Engineers (ASME) Y14.36M-1996 Surface Texture Symbols (incorporated herein by reference in its entirety). The smooth outer surface is an improvement over the non-smooth outer surfaces of knitted or braided cords (e.g. made from cotton) which are subject to tearing and shredding during its insertion and removal from periodontal sulcus 304. Therefore, the disclosed retraction cord 100 reduces tissue trauma, bleeding, and post-operative patient discomfort. Compared to knitted or braided cords, the disclosed retraction cord 100 is easier to place because it does not unravel or fray and the core 101 helps the retraction cord 100 retain the deformations imparted to it by the packing tool so that it stays in the sulcus 304. In addition, the presence of the thermoplastic 102 allows the retraction cord 100 to be made without the presence of chemically impregnated additives such as a hemostatic agent. In one embodiment, the retraction cord 100 consists of the core 101 and the thermoplastic 102. As used herein, the term "chemically impregnated" refers to the penetration of the aforementioned additives into the core 101, thermoplastic 102, or both. Exemplary hemostatic agents include, without limitation, aluminum potassium sulfate, aluminum sulfate, aluminum chloride, ferric sulfate, inorganic salts of organic vasoconstrictors such as epinephrine (R or S enantiomers or racemic mixtures thereof) and pseudoephedrine, and Visine®. Thus, the retraction cord 100 may be used on chemically sensitive patients and their previously experienced adverse chemical side effects caused by chemically impregnated cords can be avoided. The thermoplastic 102 coats at least 70%, preferably at least 80%, more preferably at least 99% of the outer surface and both ends of the core 101.

A shape of the cross-section of each of the core 101 and the thermoplastic 102 may independently be circular, polygonal (e.g. rectangular, triangular, hexagonal), elliptical, or oval, preferably circular (FIG. 1). A length of the retraction cord 100 is unlimited and may be determined in accordance with packing and winding requirements or restrictions, and the intended use of the cord 100. A diameter of the retraction cord 100 may be in a range of 0.5-3.0 mm, preferably 0.5-2.5 mm, more preferably 1.0-2.0 mm. As used herein, the term "diameter" refers to the longest distance measured between two points on the perimeter of the cross-section of the retraction cord 100 (or the core 101). A diameter of the core 101 may be in a range of 0.25-2.1 mm, preferably 0.25-1.5 mm, more preferably 0.5-0.75 mm. A ratio of the diameter of the retraction cord 100 the diameter of the core 101 is in a range of 7:6 to 10:1, preferably 2:1 to 7:1, more preferably 2:1 to 4:1. A weight of the core 101 is 10-90 wt % of the retraction cord 100, preferably 40-90 wt %, more preferably 50-80 wt %, based on a total weight of the retraction cord 100. A weight of the thermoplastic 102 is 10-90 wt % of the retraction cord 100, preferably 10-60 wt %, more preferably 20-50 wt %, based on the total weight of the retraction cord 100. The diameter of the retraction cord 100 is at most 10%, preferably at most 5%, more preferably in a range of 2-4% of a length of the retraction cord 100.

The core 101 comprises one or more of a metal, a polymer, or mixtures thereof. The metal may be silver, copper, aluminum, stainless steel, or mixtures thereof. Preferably, the metal is stainless steel and may comprise up to 50 wt % of silver/copper/aluminum, preferably up to 30 wt %, more preferably up to 10 wt %. In one embodiment, the metal does not contain copper. The core 101 may be a single strand of metal wire or a braided metal wire. Preferably, the core 101 is a single strand of metal wire. The polymer may be rubber, poly(methyl methacrylate), polyvinyl chloride, or mixtures thereof. Preferably, the polymer is rubber. Exemplary types of rubber include, without limitation, natural rubber and synthetic rubber (e.g. neoprene, ethylene propylene diene monomer (EPDM) rubber, silicone rubber, nitrile rubber, Viton®, butyl rubber, and polyurethane rubber). In one embodiment, both the metal and the polymer are present in a weight ratio that is in a range of 1:99 to 99:1, preferably 1:99 to 80:20, more preferably 1:99 to 30:70. In one embodiment, the core 101 may comprise a plurality of strands of the metal, a plurality of strands of the polymer, or both, which are woven, braided, or twisted together. The core 101 may comprise a total of 4-40 strands, preferably 4-28 strands, more preferably 4-20 strands. For example, the core has 16 strands: four pairs of warp strands and four pairs of filling strands. In one embodiment, the core comprises a mixture of metal strands and polymer strands, and a ratio of the number of metal strands to polymer strands may be in a range of 1:19 to 10:10, preferably 1:19 to 5:10, more preferably 1:19 to 3:17. As is well known in the art, each pair of the filling strands successively passes over and then under adjacent pairs of warp strands, and each pair of warp strands successively passes over and then under adjacent pairs of filling strands. The metal strand may be braided/weaved/twisted with the polymer strand at the same time, or it could be threaded through the braided/weaved/twisted polymer strands with a sewing needle. In one embodiment, the core 101 is made of a braided or woven strands made of any conventional material such as cotton. For instance, the cotton strands may be woven or braided together and then be coated with the thermoplastic 102 by a conventional die/extruder device. A diameter of the strands is in a range of 0.05-0.15 mm, preferably 0.1-0.15 mm, more preferably 0.1-0.12 mm. In an alternate embodiment, a conventional knitted or braided retraction cord 100 may be impregnated with the thermoplastic 102 so as to make up a cord 100 which is smooth and resistant to tearing. This embodiment may comprise 5-60 wt % of the thermoplastic 102, preferably 10-40 wt %, more preferably 20-30 wt %, based on a total weight of the retraction cord 100.

The thermoplastic 102 is preferably a biocompatible, non-toxic polymer which causes no known clinical or scientific adverse medical reactions. Exemplary biocompatible, non-toxic polymers include, without limitation, polytetrafluoroethylene (PTFE), expanded polytetrafluoroethylene (e-PTFE), polyester, nylon, or mixtures thereof. Preferably, the thermoplastic 102 is PTFE and/or e-PTFE because the non-stick property results in the cord 100 being resistant to sticking or adhering to dental materials (e.g. restorative and/or impression taking materials). PTFE materials are commercially available from, for example, DuPont. In one embodiment, the thermoplastic 102 is not liquid permeable. A thickness of the thermoplastic 102 may be in a range of 0.25-1.5 mm, preferably 0.25-1 mm, more preferably 0.5-1.25 mm. In one embodiment, the thermoplastic is not wax.

In one embodiment, the thermoplastic 102 comprises up to 80 wt % of a photo-activated shape-memory polymer, preferably up to 60 wt %, more preferably up to 50 wt %, based on the weight of the thermoplastic 102. The photo-activated shape-memory polymer switches between an elastomer and a rigid polymer by shining light of different wavelengths. This feature may allow the retraction cord 100 to retain the curvature around the tooth 301/teeth when an impression is taken. The photo-activated shape-memory polymer may be an acrylate-based polymer, such as polyacrylate, polymethacrylate, polyethylacrylate, polyurethane, a siloxane polymer, an epoxy polymer, an oxetane polymer or mixtures thereof. The photo-activated shape-memory polymer may contain a photo-reactive pendant group which forms cross-links between adjacent photo-activated shape-memory polymer chains and breaks the cross-links in response to light of different wavelengths. Hence, the restoration band 100 can be fixed into the curvature by shining ultraviolet-visible light (with a wavelength 260-700 nm) and then recover the original shape when exposed to light with a wavelength in the far-UV region (10-200 nm) to facilitate removal. Exemplary photo-reactive groups include, without limitation, cinnamic, coumarin, stilbene, vinylene, chalcone, thymine, and derivatives thereof. The photo-activated shape-memory polymer may be blended with the aforementioned thermoplastic 102 in an extruder (for example, in a compound extrusion process) thereby forming a polymer blend which then coats the core 101.

In another embodiment, the thermoplastic 102 comprises up to 80 wt % of a superabsorbent polymer, preferably up to 60 wt %, more preferably up to 50 wt %, based on the weight of the thermoplastic 102. The superabsorbent polymer may absorb and retain fluids (e.g. saliva, blood, water) present near the tooth 301 and then swell to open the sulcus 304 greater than the original diameter of the cord 100 so that the margin is visible for impression taking. The expanded retraction cord 100 may also compress the gum tissue 302 and stop any bleeding. The expanded diameter of the cord 100 may be in a range of 0.55-3.5 mm, more preferably from about 0.55-3.0 mm, and most preferably from about 1.05-2.5 mm. The superabsorbent polymer may comprise polyacrylate, polyacrylic, polyacrylamide, polyvinyl alcohol, polyacrylonitrile, polyethylene glycol, or mixtures thereof. In other embodiments, the superabsorbent polymer may be sodium polyacrylate, potassium polyacrylate, lithium polyacrylate, ammonium polyacrylate, or mixtures thereof. The superabsorbent polymer may be blended with the aforementioned thermoplastic 102 in an extruder thereby forming a polymer blend which then coats the core 101.

Exemplary techniques to coat the core 101 with the thermoplastic 102 include, without limitation, extrusion coating, electrostatic spray, fluidized bed coating, and dip coating.

Figure 3:
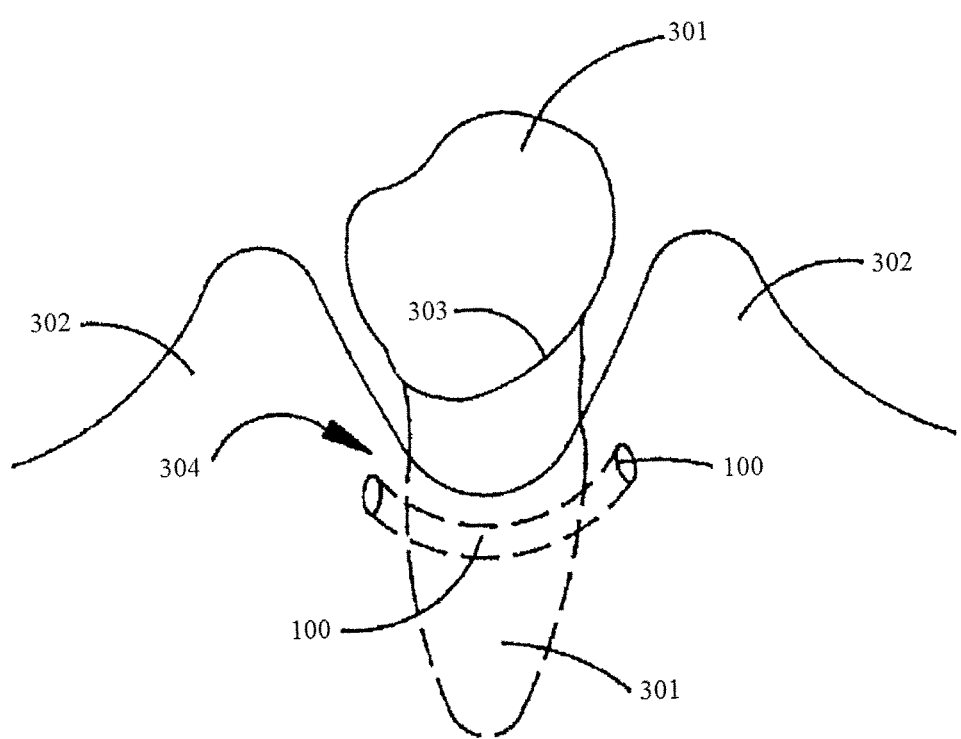
FIG. 3 is a front view of a tooth and its adjacent gum tissue, where an embodiment of a dental retraction elongated member is disposed in the periodontal sulcus to retract the gum tissue from the tooth surface.
Figure 4:
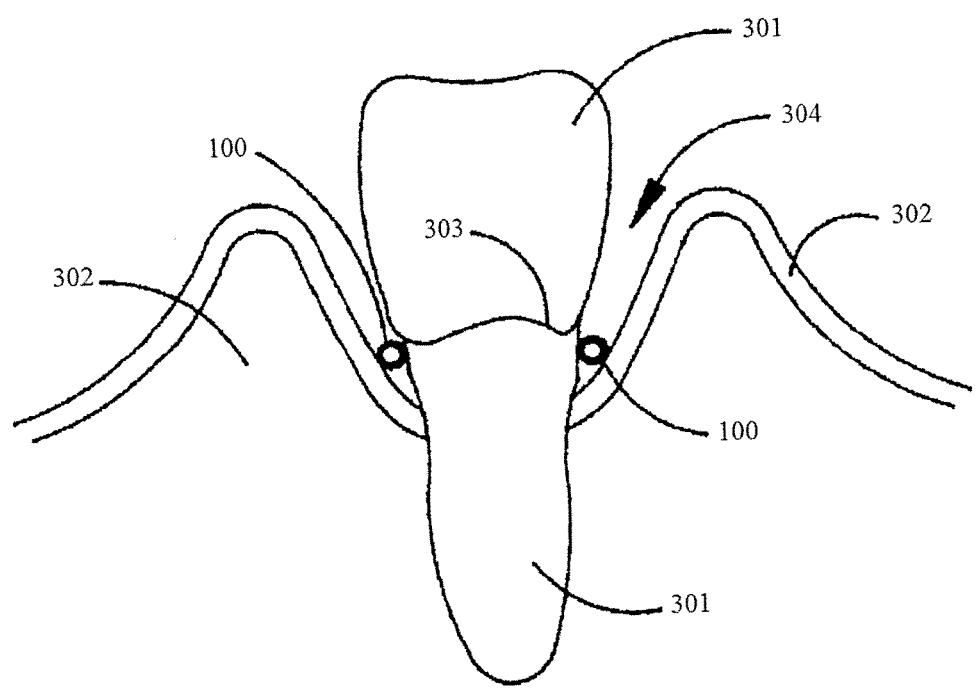
FIG. 4 is a cross-sectional side view of the dental retraction elongated member according to embodiment in FIG. 3, where the dental retraction elongated member is positioned in the periodontal sulcus between a tooth and its adjacent gum tissue so as to reflect or retract the gum tissue from the tooth surface.

The retraction cord 100 may be utilized by practitioners (e.g. dentists) as illustrated in FIGS. 3 and 4 in both prosthetic and restorative dentistry. In restorative dentistry, for example, when restoration of dental caries at, near, or below the marginal attached gingiva (i.e. gum line) is required, it is necessary to distend and retract the adjacent gum tissue 302 in order to achieve adequate access to the carious lesion. Such access allows successful removal of caries and placement of fillings (e.g. VLC composite resins or amalgams).

Figure 5:
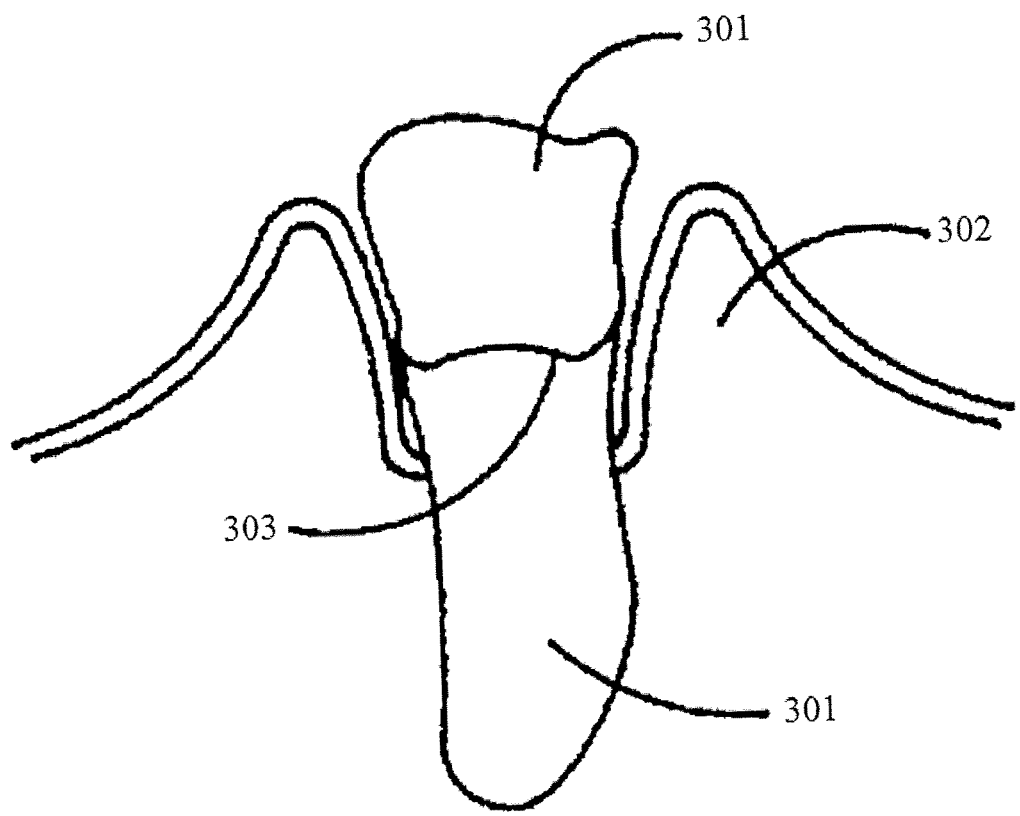
FIG. 5 is a cross-sectional side view of a tooth and its adjacent gum in a non-retracted state.

The retraction cord 100 may also be used in prosthetic dentistry involving the construction of crowns, caps, bridge works, dentures, implants, and the like. In prosthetic dentistry, it is imperative that accurate impressions or molds of a tooth 301, teeth, or implant be obtained for which prosthetics will subsequently be fabricated at a dental laboratory. At the interface of the tooth surface and gum line, it is important that prior to impression taking that the gingival sulcus 304 be retracted so that an accurate impression of the prepared tooth structure can be made. Additionally, the limit line 303 must remain uncovered, accessible, and clear of fluid and humidity. FIG. 5 illustrates a tooth 301 in unretracted form with gum tissue 302.

Figure 6:
FIG. 6 is a drawing of a retraction cord packer.

In order to uncover preparation limit line 303, the flexible retraction cord 100 as shown in FIGS. 3 and 4 is pressed into the periodontal sulcus 304 surrounding tooth 301 prior to flowing the impression taking material onto the tooth 301 or teeth with conventional techniques and tools such as a cord packer shown in FIG. 6. The disposition of the retraction cord 100 within the periodontal sulcus 304 retracts gum tissue 302 from the tooth structure to be worked on so as to ensure adequate visibility of and access to the surface of tooth 301 and allows limit line 303 to remain uncovered, accessible, and substantially free of body fluids.

Once the impression material hardens and is removed from the patient's mouth, the retraction cord 100 may be removed from the periodontal sulcus 304 by conventional methods known in the art and discarded.

For distributing purposes, the retraction cord 100 may be wound on a spool and packaged in a dispensing container. The retraction cord 100 may be cut into suitable lengths with an orthodontic wire cutter. Various retraction cords having the aforementioned diameters can also be assembled into kits that can be provided to dental practitioners. A kit comprising retraction cords in multiple sizes is useful because the sizes and shapes of teeth and gum lines can vary from patient to patient. By providing the kit with multiple embodiments of the retraction cord 100, a practitioner is able to selectively use the retraction cord 100 that is most appropriately configured in size to retract the gum from different tooth structures such as incisors, canine teeth, premolars, and molars. These kits may also comprise a cord packer.

The invention claimed is:

1. A flexible dental retraction elongated member comprising:
    a core consisting essentially of a single strand of stainless steel wire or braided, weaved, or twisted stainless steel wires; and
    an exterior thermoplastic coating comprising polytetrafluoroethylene (PTFE) or expanded polytetrafluoroethylene (e-PTFE) that does not swell when contacted with moisture,
    wherein the coating covers the core and is irreversibly attached to the core with an adhesive,
    wherein a diameter of the dental retraction elongated member ranges from 0.5 to 3.0 mm,
    wherein a ratio of the diameter of the dental retraction elongated member to a diameter of the core is from 7:6 to 10:1;
    wherein the dental retraction elongated member has a Young's modulus ranging from 1 to 100 GPa, is bendable and remains bent after being bent, and is configured to be placed between a tooth and adjacent gum tissue.

2. The dental retraction elongated member of claim 1, wherein the core consists of a single strand of stainless steel wire.

3. The dental retraction elongated member of claim 1, wherein the core consists of braided, weaved, or twisted stainless steel wires.

4. The dental retraction elongated member of claim 3, which has a circular or oval cross-section.

5. The dental retraction elongated member of claim 1, wherein the adhesive is a silicone adhesive.

6. The dental retraction elongated member of claim 1, wherein the adhesive is an epoxy adhesive.

7. The dental retraction elongated member of claim 1, wherein the adhesive is a collagen-based or plant-based adhesive.

8. The dental retraction elongated member of claim 1, wherein the adhesive crosslinks the core to the exterior thermoplastic coating.

9. The dental retraction elongated member of claim 1, wherein the ratio of the diameter of the dental retraction elongated member to a diameter of the core ranges from 2:1 to 4:1; and wherein the member has a Young's modulus ranging from 5 to 20 GPa.

10. A method for retracting gingival tissue comprising placing the dental retraction elongated member of claim 1 between at least one tooth and adjacent gingival sulcus and bending or deforming the dental retraction elongated member to retract the gingival sulcus from the tooth.

11. The method of claim 10, wherein the adhesive in the dental retraction member is a silicone adhesive.

12. The method of claim 10, wherein the adhesive in the dental retraction member is an epoxy adhesive.

13. The method of claim 10, wherein the ratio of the diameter of the dental retraction elongated member to a diameter of the core ranges from 2:1 to 4:1; and wherein the member has a Young's modulus ranging from 5 to 20 GPa.

14. A kit comprising at least one dental retraction elongated member of claim 1 and a retraction cord packer.

15. A flexible dental retraction elongated member comprising:
    a core consisting essentially of a single strand of stainless steel wire; braided, weaved or twisted stainless steel wires; or braided, weaved or twisted Stainless steel wires and polymer strands;
    an exterior thermoplastic coating comprising polytetrafluoroethylene (PTFE) or expanded polytetrafluoroethylene (e-PTFE) that ranges in thickness from 0.25 to 1.5 mm;
    wherein the coating covers the core and is irreversibly attached to the core with an adhesive;
    wherein a diameter of the dental retraction elongated member ranges from 0.5 to 3.0 mm,
    wherein a ratio of the diameter of the dental retraction elongated member to a diameter of the core is from 2:1 to 4:1;
    wherein the member has a Young's modulus ranging from 5 to 20 GPa, is bendable and remains bent after being bent, and is configured to be placed between a tooth and adjacent gum tissue.

16. The flexible dental retraction elongated member of claim 15 that is not chemically impregnated.

17. The flexible dental retraction elongated member of claim 15, wherein the core consists of the single strand of stainless steel metal wire.

18. The flexible dental retraction elongated member of claim 15, wherein the core consists of braided, weaved, or twisted stainless steel metal wires.

19. The dental retraction elongated member of claim 15, wherein the adhesive is a silicone adhesive.

20. The dental retraction elongated member of claim 15, wherein the adhesive is an epoxy adhesive.

* * * * *